United States Patent [19]

Mueller et al.

[11] Patent Number: 5,631,003
[45] Date of Patent: May 20, 1997

[54] HAIR TREATMENT PREPARTATION

[75] Inventors: Reinhard Mueller, Erkelenz; Kurt Seidel, Duesseldorf; Detlef Hollenberg, Erkrath, all of Germany

[73] Assignee: Henkel Kommanditgesellschaft auf Aktien, Duesseldorf, Germany

[21] Appl. No.: 540,334

[22] Filed: Oct. 6, 1995

Related U.S. Application Data

[63] Continuation of Ser. No. 211,258, filed as PCT/EP92/02118, Sep. 16, 1992, published as WO93/05756, Apr. 1, 1993, abandoned.

[30] Foreign Application Priority Data

Sep. 25, 1991 [DE] Germany ............ 41 31 898.6

[51] Int. Cl.$^6$ ................... A61K 7/08
[52] U.S. Cl. ............ 424/70.31; 424/70.1; 424/70.11
[58] Field of Search ................ 424/70.1, 70.11, 424/70.31

[56] References Cited

U.S. PATENT DOCUMENTS

| | | | |
|---|---|---|---|
| 3,235,457 | 2/1966 | Laden | 157/85 |
| 3,472,840 | 10/1969 | Stone et al. | 260/231 |
| 3,547,828 | 12/1970 | Mansfied et al. | 252/351 |
| 3,707,535 | 12/1972 | Lew | 260/210 R |
| 3,816,616 | 6/1974 | Anguillo et al. | 424/70 |
| 3,839,318 | 10/1974 | Mansfield | 260/210 R |
| 3,878,247 | 4/1975 | Moss et al. | 260/561 N |
| 4,374,125 | 2/1983 | Newell | 424/70 |
| 4,744,977 | 5/1988 | Hensen et al. | 424/70 |
| 4,865,774 | 9/1989 | Fabry et al. | 252/554 |
| 4,931,218 | 6/1990 | Schenker et al. | 252/551 |

FOREIGN PATENT DOCUMENTS

| | | |
|---|---|---|
| 0077167 | 4/1983 | European Pat. Off. . |
| 0356665 | 3/1990 | European Pat. Off. . |
| 1943689 | 3/1970 | Germany . |
| 2036472 | 2/1971 | Germany . |
| 2150557 | 6/1972 | Germany . |
| 2537378 | 3/1976 | Germany . |
| 2811010 | 9/1978 | Germany . |
| 2817369 | 10/1978 | Germany . |
| 2819735 | 11/1979 | Germany . |
| 2836520 | 2/1980 | Germany . |
| 3044738 | 6/1981 | Germany . |
| 3001064 | 7/1981 | Germany . |
| 3301121 | 7/1983 | Germany . |
| 3244274 | 5/1984 | Germany . |
| 3330326 | 3/1985 | Germany . |
| 3402599 | 9/1985 | Germany . |
| 3442175 | 5/1986 | Germany . |
| 3708451 | 10/1988 | Germany . |
| 3723354 | 1/1989 | Germany . |
| 3725030 | 2/1989 | Germany . |
| 3926344 | 2/1991 | Germany . |
| 3929973 | 3/1991 | Germany . |
| 2104091 | 3/1983 | United Kingdom . |
| 9103229 | 3/1991 | WIPO . |
| WO91/03229 | 3/1991 | WIPO . |

*Primary Examiner*—Jyothsna Venkat
*Attorney, Agent, or Firm*—Ernest G. Szoke; Wayne C. Jaeschke; Real J. Grandmaison

[57] ABSTRACT

Hair treatment compositions containing a combination of a zwitterionic polymer and a derivative of 2-pyrrolidone. Such preparations improve the condition of the hair, in particular the moisture retention and curl retention capability after cleaning or cosmetic treatment. In addition, the preparations are better tolerated by the skin.

17 Claims, No Drawings

HAIR TREATMENT PREPARTATION

This application is a continuation, of application Ser. No. 08/211,258, filed as PCT/EP92/02118 Sep. 16, 1992 published as WO93/05756 Apr. 1, 1993 now abandoned.

FIELD OF THE INVENTION

This invention relates to hair treatment preparations containing a combination of a zwitterionic polymer and a pyrrolidone carboxylic acid.

STATEMENT OF RELATED ART

Any cleaning or cosmetic treatment of the hair affects its natural structure. The result of this is that, after such a treatment, for example washing, dyeing or permanent waving, the hair often shows a number of unsatisfactory properties in addition to the desired changes. Besides a deterioration in wet and dry combability, these unsatisfactory properties include electrostatic charging and inadequate moisture retention. In many cases, the curl retention capacity of the dry hair is also unsatisfactory. In addition, it is desirable that the scalp remain largely unaffected by the treatment.

To remedy the situation, corresponding components either have to be added to the hair treatment preparations, or the hair has to be subsequently subjected to a separate treatment with substances which are normally formulated as a rinse.

Polymeric compounds, more particularly cationic, anionic and zwitterionic polymers, are often used as such substances to improve the properties of hair. Corresponding polymers are described, for example, in U.S. Pat. Nos. 3,816,616, 3,472,840, DE-A-21 50 557, DE-A-28 17 369, DE-A-28 11 010, DE-A-33 01 121, DE-A-30 44 738, DE-A-37 08 451, GB-B-2,104,091 and DE-A-39 29 973.

2-Pyrrolidone-5-carboxylic acid is a constituent of the so-called natural moisturizing factor ("NMF") of the skin. Accordingly, this compound or its sodium salt is used as a moisturizer for skin creams and other cosmetic products. In addition, it is known that the salts increase the softness and elasticity of the horny layer and the surface of hair fibers (H. P. Fiedler, *Lexikon der Hilfsstoffe für Pharmazie, Kosmetik und angrenzende Gebiete* [Title in English: Dictionary of Auxiliary Substances for Pharmacy, Cosmetology, and Adjoining Fields], 3rd Edition, [Editio Canto Aulendorf, 1989], pages 110, 111).

DESCRIPTION OF THE INVENTION

Summary of the Invention

It has now been found that the effects of both classes of compounds in hair treatment preparations are synergistically enhanced if these compounds are used in combination with one another.

Accordingly, the present invention relates to preparations containing typical constituents for the treatment of hair, characterized in that they contain a combination of A) a zwitterionic polymer and B) a compound corresponding to general formula (I):

in which at least one of the substituents $R^1$ to $R^3$ is a group $-COOR^4$, where $R^4$ is hydrogen, an alkali metal ion, an alkaline earth metal ion or an ammonium ion $^+NHR^5R^6R^7$, where $R^5$ to $R^7$ independently of one another represent hydrogen, alkyl groups having 1 to 22 carbon atoms, hydroxyalkyl groups having 1 to 4 carbon atoms, alkenyl groups having 2 to 22 carbon atoms, acyl groups having 2 to 22 carbon atoms or aromatic groups, optionally substituted, having 6 to 10 carbon atoms, and the remaining substituents $R^1$ to $R^3$ represent hydrogen or alkyl groups having 1 to 4 carbon atoms.

Description of Preferred Embodiments

In the context of the invention, zwitterionic polymers are polymers which contain both cationic groups and anionic groups or groups readily convertible into such groups.

Cationic groups are, for example, groups having at least one ammonium or phosphonium unit. Examples of a group readily convertible into a cationic group are primary, secondary and in particular tertiary amino groups. Ammonium groups are preferred cationic groups.

Suitable anionic groups are, for example, carboxylic acid, sulfonic acid and phosphoric acid groups in free form or in salt form. The carboxylic acid groups and their alkali metal, alkaline earth metal, aluminum and ammonium salts are preferred anionic groups.

The polymers used in accordance with the invention may be produced from monomers having both cationic and anionic groups. In this case, the polymers may consist of a single type of monomer. However, copolymers of the monomers mentioned and other nonionic monomers may also be used. Such nonionic monomers may be, for example, vinyl-based esters and amides, such as methyl acrylate, ethyl acrylate, methyl methacrylate, ethyl methacrylate, hydroxypropyl methacrylate and acrylamide. These copolymers preferably contain at least 20% and, more preferably, at least 50%, of ionic monomers.

Polymers preferably used in accordance with the invention are produced from at least two ionic monomers, a cationic monomer and an anionic monomer. Cationic and anionic monomers may be present in a molar ratio of 1:1. However, monomers of one type, more particularly the cationic monomers, are preferably used in excess. Cationic and anionic monomers are generally used in a ratio of 95:5 to 60:40. In addition, the polymers may contain nonionic monomers of the type mentioned above in quantities of up to 50 mole-% and, more particularly, in quantities of up to 20 mole-%.

The zwitterionic polymers described in DE-A-39 29 973 are preferred for the purposes of the invention. These zwitterionic polymers are essentially composed of α) monomers having quaternary ammonium groups corresponding to general formula (II):

$$R^8-CH=CR^9-CO-Z-(C_nH_{2n})-N^{(+)}R^{10}R^{11}R^{12} A^{(-)} \quad (II),$$

in which $R^8$ and $R^9$ independently of one another represent hydrogen or a methyl group and $R^{10}$, $R^{11}$ and $R^{12}$ independently of one another represent alkyl groups having 1 to 4 carbon atoms, Z is an NH group or an oxygen atom, n is an integer of 2 to 5 and $A^{(-)}$ is the anion of an organic or inorganic acid
and β) monomeric carboxylic acids corresponding to general formula (III):

$$R^{13}-CH=CR^{14}-COOH \quad (III),$$

in which $R^{13}$ and $R^{14}$ independently of one another represent hydrogen or methyl groups, or alkali metal, alkaline earth metal, aluminum or ammonium salts of these acids.

Suitable starting monomers for the monomers (α) are, for example, dimethylaminoethyl acrylamide, dimethylaminoethyl methacrylamide, dimethylaminopropyl acrylamide, dimethylaminopropyl methacrylamide and diethylaminoethyl acrylamide, where Z is an NH group, or dimethylaminoethyl acrylate, dimethylaminoethyl methacrylate and diethylaminoethyl acrylate, where Z is an oxygen atom.

The monomers mentioned are prepared by known methods as described, for example, in U.S. Pat. No. 3,878,247, DE-C-28 19 735, DE-C-28 36 520, DE-C-34 02 599 or CH 464 891.

The monomers containing a tertiary amino group are then quaternized in known manner, methyl chloride, dimethyl sulfate or diethyl sulfate being particularly suitable alkylating agents. The quaternization reaction may be carried out in aqueous solution or in a solvent. Suitable methods are described, for example, in DE-A-33 30 326, DE-A-25 37 378 and DE-A-32 44 274.

Monomers of formula (II) which are derivatives of acrylamide or methacrylamide are advantageously used. Monomers containing halide, methoxysulfate or ethoxysulfate ions as counterions are also preferred, as are monomers corresponding to formula (II) in which $R^{10}$, $R^{11}$ and $R^{12}$ are methyl groups.

Acrylamidopropyl trimethyl ammonium chloride is a most particularly preferred monomer of formula (II).

Monomeric carboxylic acids (β) are acrylic acid, methacrylic acid, crotonic acid and 2-methyl crotonic acid. Acrylic acid or methacrylic acid, more particularly acrylic acid, is preferably used. Preferred salts of these carboxylic acids are the lithium, sodium, potassium, magnesium, calcium and aluminum salts. The sodium salt is particularly preferred. The ammonium salts in which the ammonium ion may contain one to three alkyl groups having 1 to 4 carbon atoms or hydroxyalkyl groups having 2 to 4 carbon atoms as substituents may also be used. Salts containing unsubstituted ammonium ions and triethanolammonium ions are preferred.

So far as the preparation of these zwitterionic polymers is concerned, specific reference is made to the disclosure of DE-A-39 29 973.

The compounds of general formula (I) are derivatives of 2-pyrrolidone.

Preferred derivatives are 2-pyrrolidone-3-, -4- and -5-carboxylic acid and salts thereof. Preferred salts of these compounds are the sodium, potassium, calcium, magnesium and ammonium salts, in which the ammonium ion contains 1 to 3 $C_{1-4}$ alkyl group in addition to hydrogen.

Particularly preferred compounds of general formula (I) are 2-pyrrolidone-5-carboxylic acid and salts thereof. The sodium salt is most particularly preferred.

The zwitterionic polymers are present in the preparations according to the invention in quantities of preferably 0.1 to 10% by weight, based on the preparation as a whole. Concentrations of 0.2 to 5% by weight are particularly preferred.

The compounds corresponding to formula (I) are present in the preparations according to the invention in quantities of preferably 0.1 to 15% by weight and, more preferably, 0.5 to 10% by weight, based on the preparation as a whole.

In addition to the zwitterionic polymers and compounds corresponding to general formula (I), the preparations according to the invention may contain any of the constituents typically encountered in hair treatment preparations. The nature of the preparation determines which of the constituents mentioned in the following are present therein.

Most hair treatment preparations, such as shampoos, rinses, permanent wave lotions, hair dyes and hair tints, are aqueous preparations containing surfactants. The surfactants used are anionic, cationic, zwitterionic, amphoteric and/or nonionic surfactants.

Anionic surfactants suitable for use in the hair treatment preparations according to the invention are any of the anionic surfactants which are suitable for use on the human body. They are characterized by a water-solubilizing anionic group, for example a carboxylate, sulfate, sulfonate or phosphate group, and a lipophilic alkyl group having approximately 10 to 22 carbon atoms. Glycol or polyglycol ether groups, ester, ether and amide groups and hydroxyl groups may also be present in the molecule. The following are examples of suitable anionic surfactants in the form of the sodium, potassium and ammonium salts and also the mono-, di- and trialkanolammonium salts having 2 or 3 carbon atoms in the alkanol group:

linear fatty acids having 10 to 22 carbon atoms (soaps),
ether carboxylic acids corresponding to the formula R—O—$(CH_2-CH_2O)_x$—$CH_2$—COOH, in which R is a linear alkyl group having 10 to 22 carbon atoms and x=0 or 1 to 10,
acyl sarcosides having 10 to 18 carbon atoms in the acyl group,
acyl taurides having 10 to 18 carbon atoms in the acyl group,
acyl isethionates having 10 to 18 carbon atoms in the acyl group,
sulfosuccinic acid mono- and dialkyl esters having 8 to 18 carbon atoms in the alkyl group and sulfosuccinic acid monoalkyl polyoxyethyl esters having 8 to 18 carbon atoms in the alkyl group and 1 to 6 oxyethyl groups,
linear alkane sulfonates having 12 to 18 carbon atoms,
linear alpha-olefin sulfonates having 12 to 18 carbon atoms,
alpha-sulfofatty acid methyl esters of fatty acids having 12 to 18 carbon atoms,
alkyl sulfates and alkyl polyglycol ether sulfates corresponding to the formula R—$O(CH_2-CH_2O)_x$—$OSO_3H$, in which R is a preferably linear alkyl group having 10 to 18 carbon atoms and x=0 or 1 to 12,
mixtures of surface-active hydroxysulfonates according to DE-A-37 25 030,
sulfated hydroxyalkyl polyethylene and/or hydroxyalkylene propylene glycol ethers according to DE-A-37 23 354,
sulfonates of unsaturated fatty acids having 12 to 24 carbon atoms and 1 to 6 double bonds according to DE-A-39 26 344,
esters of tartaric acid and citric acid with alcohols which are adducts of approximately 2 to 15 molecules of ethylene oxide and/or propylene oxide with fatty alcohols having 8 to 22 carbon atoms.

Preferred anionic surfactants are alkyl sulfates and alkyl polyglycol ether sulfates having 10 to 18 carbon atoms in the alkyl group and up to 12 glycol ether groups in the molecule.

Shampoos based on anionic surfactants are preferred hair treatment preparations according to the invention.

Preferred cationic surfactants in the hair treatment preparations according to the invention are quaternary ammonium compounds, such as alkyl trimethyl ammonium chlorides, dialkyl dimethyl ammonium chloride and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethylbenzyl ammonium chloride and tricetyl methyl ammonium chloride. Examples of other suitable cationic surfactants are cetyl pyridinium chloride, tallow alkyl tris-(oligooxyalkyl)-ammonium phosphate and the compounds disclosed in DE-A-34 42 175.

Hair rinses based on cationic surfactants are also preferred hair treatment preparations according to the invention.

Zwitterionic surfactants are surface-active compounds which contain at least one quaternary ammonium group and at least one $—COO^{(-)}$ or $—SO_3^{(-)}$ group in the molecule. Particularly suitable zwitterionic surfactants are the so-called betaines, such as N-alkyl-N,N-dimethyl ammonium glycinates, for example coconut oil alkyl dimethyl ammonium glycinate, N-acyl aminopropyl-N,N-dimethyl ammonium glycinates, for example coconut oil acylaminopropyl dimethyl ammonium glycinate, and 2-alkyl-3-carboxymethyl-3-hydroxyethyl imidazolines having 8 to 18 carbon atoms in the alkyl or acyl group and also coconut oil acylaminoethyl hydroxyethylcarboxymethyl glycinate. A preferred zwitterionic surfactant is the fatty acid amide derivative known by the CTFA name of Cocamidopropyl Betaine.

Ampholytic surfactants are surface-active compounds which, in addition to a $C_{8-18}$ alkyl or acyl group, contain at least one free amino group and at least one —COOH or —$SO_3H$ group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids having approximately 8 to 18 carbon atoms in the alkyl group. Particularly preferred ampholytic surfactants are N-coconut oil alkylaminopropionate, coconut oil acylaminoethyl aminopropionate and $C_{12-18}$ acyl sarcosine.

Nonionic surfactants contain, for example, a polyol group, a polyalkylene glycol ether group or a combination of polyol and polyglycol ether groups as their hydrophilic group. Such compounds are, for example, adducts of 2 to 30 moles of ethylene oxide and/or 0 to 5 molecules of propylene oxide with linear fatty alcohols having 8 to 22 carbon atoms, with fatty acids having 12 to 22 carbon atoms and with alkylphenols having 8 to 15 carbon atoms in the alkyl group, $C_{12-22}$ fatty acid monoesters and diesters of adducts of 1 to 30 molecules of ethylene oxide with glycerol, glycerol monoesters and diesters and sorbitan monoesters and diesters of saturated and unsaturated $C_{8-22}$ fatty acids and ethylene oxide adducts thereof, $C_{8-22}$ alkyl mono- and oligoglycosides and ethoxylated analogs thereof and adducts of 5 to 60 moles of ethylene oxide with castor oil and hydrogenated castor oil.

Particularly preferred nonionic surfactants are $C_{8-22}$ alkyl mono- and oligoglycosides, of which the production and use as surfactants are known, for example, from U.S. Pat. Nos. 3,839,318, 3,707,535, 3,547,828, DE-A-19 43 689, DE-A-20 36 472 and DE-A-30 01 064 and from EP-A-77 167. They are prepared in particular by reaction of glucose or oligosaccharides with primary alcohols having 8 to 22 carbon atoms. So far as the glycoside component is concerned, both monoglycosides in which a cyclic sugar unit is attached to the fatty alcohol by a glycoside bond and oligomeric glycosides having a degree of oligomerization of up to preferably about 8 are suitable. Degrees of oligomerization of 1.4 and lower are particularly preferred. The degree of oligomerization is a statistical mean value on which a homolog distribution typical of such products is based.

It has been found that the effect of the combination according to the invention is further enhanced if the hair treatment preparation additionally contains a nonionic surfactant. This is particularly the case where the nonionic surfactant is a $C_{8-22}$ alkyl mono- and -oligoglycoside.

Accordingly, preparations additionally having a nonionic surfactant, more particularly a $C_{8-22}$ alkyl mono- and -oligoglucoside, are preferred for the purposes of the invention.

The compounds having alkyl groups used as surfactants may be individual substances. However, these substances are preferably produced from natural vegetable and animal starting materials so that mixtures of substances differing in their alkyl chain lengths according to the particular starting materials are obtained.

The surfactants formed by adducts of ethylene and/or propylene oxide with fatty alcohols or derivatives of these adducts may be both normal-range products and also narrow-range products. Normal-range products are understood to be mixtures of homologs which are obtained in the reaction of fatty alcohol and alkylene oxide using alkali metals, alkali metal hydroxides or alkali metal alcoholates as catalysts. By contrast, narrow-range products are obtained when, for example, hydrotalcites, alkaline earth metal salts of ether carboxylic acids, alkaline earth metal oxides, hydroxides or alcoholates are used as catalysts. It may be preferable to use narrow-range products.

The preparations according to the invention preferably contain surface-active compounds in quantities of 0.1 to 50% by weight, based on the preparation as a whole.

Other typical constituents of hair treatment preparations are:

cationic, anionic and nonionic polymers, such as for example quaternized cellulose ethers, polysiloxanes, vinyl pyrrolidone copolymers, acrylamide/dimethyl diallyl ammonium chloride copolymers, vinyl acetate/crotonic acid copolymers, polyvinyl pyrrolidone and polyacrylic acids;

thickeners, such as for example cellulose ethers, uncrosslinked and polyol-crosslinked polyacrylic acids, agar-agar, guar gum, alginates and xanthan gums;

protein hydrolyzates, more particularly elastin and collagen hydrolyzates;

perfume oils;

solubilizers, such as ethanol, isopropanol, ethylene glycol, propylene glycol, glycerol and diethylene glycol;

dyes;

substantive dyes for dyeing and tinting the hair;

oxidation dye precursors (primary intermediate and coupler components) for dyeing and tinting the hair;

reducing agents, such as thioglycolic acid, for splitting the disulfide bridges in permanent waving;

oxidizing agents, such as potassium bromate and hydrogen peroxide, for fixing in permanent waving;

antidandruff agents, such as piroctone olamine and zinc omadine;

pH regulators, such as citric acid/sodium citrate buffer;

active substances, such as panthenol, allantoin, vegetable extracts and vitamins;

light stabilizers;
consistency regulators, such as sugar esters, polyol esters or polyol alkylethers;
fats and waxes, such as spermaceti, beeswax, montan wax, paraffins and fatty alcohols;
superfatting agents, such as polyethoxylated lanolin derivatives, lecithin derivatives and fatty acid alkanolamides;
complexing agents, such as EDTA and phosphonic acids;
swelling and penetration agents, such as glycerol, propylene glycol monoethyl ether, guanidines and urea;
opacifiers, such as latex;
pearlescers, such as ethylene glycol mono- and -distearate;
propellents, such as propane/butane mixtures, $N_2O$, dimethyl ether and air; and
antioxidants.

The preparations according to the invention have a pH value preferably in the range from 3.5 to 10 and more preferably in the range from 4.5 to 9.

Hair treatment products in which the preparations according to the invention may be used are, for example, shampoos, shower baths, rinses, hair dyes, hair tints, permanent wave preparations, permanent wave fixing preparations, setting lotions, setting gels, hair tonics, hair creams and hair lotions.

These hair treatment products may be formulated as typical hair treatment preparations, for example in the form of an aqueous solution or emulsion, an aqueous-alcoholic or alcoholic solution, a cream, a gel, a lotion or an aerosol.

The present invention also relates to the use of the preparations according to the invention for the treatment of hair and more particularly for the washing and care of hair. This encompasses both treatments in which the hair is rinsed after the treatment and treatments in which the preparation remains on the hair. The preparations according to the invention have proved to be particularly advantageous in cases where the hair is rinsed after a certain contact time of the treatment preparation.

EXAMPLES

Shampoos of the following composition (in % by weight) were used for the tests:

The moisture retention capacity, the curl retention capacity and the swelling of pig epidermis, which is a measure of the skin compatibility of the preparation, were determined.

1. Moisture Retention Capacity

The moisture retention capacity is a measure of the extent to which the hair retains its natural water content in a dry environment.

The measurement was carried out on standardized mid-brown European hair (Alkinco 6634; tress weight: 2 g).

Pretreatment:

The hair tresses were first washed with an aqueous solution of Texapon N25 (12% of active substance) and dried in air.

Determination of the zero value:

The hair tresses were left for 24 hours at room temperature/95% relative air humidity. The weight of the hair determined thereafter was recorded as $m_H$. The hair tresses were then dried over phosphorus pentoxide for 24 hours at room temperature. The quantity of water given off from the hair, which was determined from the increase in the weight of the phosphorus pentoxide, was recorded as $m_W$. Finally, the hair tresses were redried for about 30 minutes at 50° C. in a recirculating air drying cabinet to constant weight; the weight of the dry hair was recorded as $m_{Ho}$.

Measurement:

The same hair tresses were treated for 5 minutes with the shampoo and then rinsed with water for 30 seconds. This operation was repeated five times. The variables $m_H$, $m_W$ and $m_{Ho}$ were then determined in the same way as the zero value.

15 Hair tresses were used for each measurement.

The results of the measurements are set out in Table 1:

Water absorption $(m_H - m_{Ho})$

Residual water content $(m_H - m_{Ho}) - m_W$.

The values obtained in the zero measurement (water content at 95% relative air humidity: 18% of the hair weight; water content after storage over phosphorus pentoxide: 3% of the hair weight) were put at 100%.

|  | C | S1 | S2 | S3 | S4 | S5 | S6 | S7 | S8 | S9 |
|---|---|---|---|---|---|---|---|---|---|---|
| Texapon ®N 25[1] | 9.0 | 9.0 | 9.0 | 9.0 | 9.0 | 9.0 | 9.0 | 9.0 | 9.0 | 9.0 |
| Akypo ® RLM 100 NV[2] | 3.0 | 3.0 | 3.0 | 3.0 | 3.0 | 3.0 | 3.0 | 3.0 | 3.0 | 3.0 |
| Dehyton ®K[3] | 3.0 | 3.0 | 3.0 | 3.0 | 3.0 | 3.0 | 3.0 | 3.0 | 3.0 | 3.0 |
| Nutrilan ® I[4] | 0.5 | 0.5 | 0.5 | 0.5 | 0.5 | 0.5 | 0.5 | 0.5 | 0.5 | 0.5 |
| Polymer P1[5] | — | 0.5 | 1.0 | — | — | 0.5 | 0.5 | 0.5 | 1.0 | 1.0 |
| Ajidew ®N50[6] | — | — | — | 5.0 | 10.0 | 5.0 | 10.0 | 5.0 | 5.0 | 5.0 |
| Alkyl glucoside APG-600[7] | — | — | — | — | — | — | — | 2.0 | — | 2.0 |
| Water ad | 100 | 100 | 100 | 100 | 100 | 100 | 100 | 100 | 100 | 100 |

[1]Sodium lauryl ether sulfate; CTFA name: Sodium Laureth Sulfate (approximately 28% of active substance in water) (HENKEL)
[2]$C_{12-14}$-alkyl-O—$(CH_2CH_2$—$O)_{10}$—$CH_2$—COONa (22% of active substance in water) (CHEM-Y)
[3]Fatty acid amide derivative of betaine structure with the formula R—CONH—$(CH_2)_3$—$N^+(CH_3)_2$—$CH_2$—$COO^-$; CTFA name: Cocamidopropyl Betaine (approximately 30% of active substance in water) (HENKEL)
[4]Protein hydrolyzate; CTFA name: Hydrolyzed Animal Collagen (GRÜNAU)
[5]Polymer of acrylamidopropyl trimethyl ammonium chloride and acrylic acid (molar ratio 3:1) neutralized with sodium hydroxide according to DE-A-39 29 973. Particulars of the preparation of the polymer can be found in that document.
[6]Sodium salt of dl-2-pyrrolidone-5-carboxylic acid (50% aqueous solution)(AJINOMOTO).
[7]Aqueous solution of RO(Z)$_x$ with Z = glucose, x = 1.4 and R = n-alkyl ($C_{12-14}$), (50% of active substance) (HORIZON)

TABLE 1

| Shampoo | Moisture retention capacity | |
|---|---|---|
| | Water absorption | Residual water content |
| Zero value | 100% | 100% |
| C | 100% | 100% |
| S1 | 100% | 100% |
| S3 | 109% | 113% |
| S4 | 108% | 127% |
| S5 | 110% | 121% |
| S6 | 112% | 135% |

2. Skin Compatibility Tests

The skin compatibility of the shampoos was determined by the in vitro method developed by Zeidler and Reese which is described in detail in the journal *Ärztliche Kosmetologie* [Title in English: Medical Cosmetology] 13, 39–45 (1983).

The swelling of pig epidermis was used as a measure of the skin compatibility of the shampoos. To this end, the epidermis required was taken from young pigs immediately after their slaughter and deep-cooled.

For the measurement, 1 cm×6 cm strips stamped out from the epidermis were immersed in the shampoos (diluted with water to a surfactant content of 2% by weight) which had been heated to 39° C. and adjusted to pH 6.5. The weight of the swollen strips was then determined after brief rinsing and removal of the adhering water by gentle squeezing under defined conditions. The strips were then dried over calcium chloride for 24 hours and reweighed. To eliminate any influences attributable to the specific properties of the particular animal or the point of removal (back, flank), a standard measurement was carried out in each case. To this end, an immediately adjacent epidermis strip was similarly treated with water instead of the shampoo.

The values s for the shampoo treatment and w for the treatment with water may be calculated on the basis of the following relation:

$$s, w = \frac{\text{weight (swollen epidermis)} - \text{weight (dry epidermis)}}{\text{weight (dry epidermis)}}$$

Finally, the standardized relative change in swelling S is defined as:

$$S = [(s/w) - 1] \cdot 100\%$$

By definition, therefore, the S value of the skin treated with water is 0%; negative values are indicative of swelling-inhibiting properties.

The results of the swelling measurements are set out in Table 2.

TABLE 2

| Shampoo | Changes in swelling |
|---|---|
| | S value |
| C | 50 ± 7 |
| S1 | 46 ± 6 |
| S3 | 40 ± 5 |
| S5 | 33 ± 6 |
| S7 | 24 ± 7 |

3. Curl Retention Capacity

A 15 cm long hair tress (Alkinco 6634; tress weight: 2 g) was wound onto a glass tube with an external diameter of 1.7 cm, fixed and treated with 0.2 g of the shampoo. The hair tresses were then rinsed with water and dried. A measure of the stability of the curl obtained after withdrawal of the glass rod is the curl retention value. The curl retention value is defined as $[(1-l_x)/(1-l_o)] \cdot 100\%$, where l is the length of the hair tress (15 cm), $l_o$ is the length of the hair tress immediately drying and $l_x$ is the length of the hair tress after storage in a drying cabinet for 48 h under constant conditions (30° C./40% relative air humidity). The results of the measurements are set out in Table 3.

TABLE 3

| Shampoo | Curl retention values |
|---|---|
| | Curl retention value |
| C | 87.1 |
| S2 | 94.7 |
| S3 | 85 |
| S8 | 96.2 |
| S9 | 96.8 |

4. Application Examples

| Components | % by weight |
|---|---|
| 4.1. Hair rinse | |
| Texapon ®N 25 | 5.0 |
| Dehyton ®K | 1.0 |
| Polymer P1[8] | 2.5 |
| Ajidew ®N50 | 2.0 |
| Water ad 100 | |
| 4.2. Hair rinse | |
| Texapon ®N 25 | 5.0 |
| Dehyton ®AB 30[9] | 1.0 |
| Polymer P1[8] | 3.0 |
| Ajidew ®N50 | 3.0 |
| Water ad 100 | |
| 4.3 Hair rinse | |
| Texapon ®SB 3[10] | 0.9 |
| Texapon ®K14 S spez.[11] | 1.2 |
| Dehyton ®AB 30 | 1.0 |
| Polymer P1[8] | 1.5 |
| Ajidew ®N50 | 2.0 |
| Water ad 100 | |
| 4.4. Hair rinse | |
| Texapon ®SB 3 | 1.0 |
| Dehyton ®AB 30 | 7.5 |
| Polymer P1[8] | 2.5 |
| Ajidew ®N50 | 2.0 |
| Water ad 100 | |
| 4.5. Hair rinse | |
| $C_{16-18}$ fatty alcohol | 3.0 |
| Dehyton ®K | 8.0 |
| Texapon ®N 25 | 5.0 |
| Polymer P1[8] | 2.5 |
| Ajidew ®N50 | 5.0 |
| Water ad 100 | |

[8]20% of active substance in water
[9]Fatty amine derivative of betaine structure; CTFA name: Coco-Betaine (approximately 30% of active substance in water) (HENKEL)
[10]Sulfosuccinic acid semiester based on a $C_{12-14}$alkyl poly(3-EO) glycol ether, disodium salt; CTFA name: Disodium Laureth Sulfosuccinate (40% of active substance in water) (HENKEL)
[11]Sodium lauryl myristyl ether sulfate (approximately 30% of active substance in water) (HENKEL)

To prepare this hair rinse, the mixture of surfactants and polymer was introduced into the molten fatty phase and emulsified therein.

| Components | % by weight |
|---|---|
| 4.6. Hair shampoo | |
| Texapon ®N 25 | 50.0 |
| Dehyton ®K | 10.0 |
| Polymer P1[8] | 5.0 |
| Ajidew ®N50 | 10.0 |
| Water ad 100 | |
| 4.7. Hair shampoo | |
| Texapon ®N 25 | 45.0 |
| Dehyton ®K | 15.0 |
| Akypo ®RLM 100 NV | 5.0 |
| Polymer P1[8] | 5.0 |
| Ajidew ®A 100[12] | 2.0 |
| Water ad 100 | |
| 4.8. Hair shampoo | |
| Texapon ®K14 S spez. | 15.0 |
| Texapon ®SB 3 | 12.0 |
| Ethoxylated (9 EO) palm kernel oil fatty acid | 1.0 |
| Alkyl glucoside APG-600 | 4.0 |
| Dehyton ®CB[13] | 9.7 |
| Polymer P1[8] | 3.0 |
| Ajidew ®N50 | 2.0 |
| Water ad 100 | |
| 4.9. Hair shampoo | |
| Texapon ®SB 3 | 12.0 |
| Ethoxylated (9 EO) palm kernel oil fatty acid | 1.0 |
| Dehyton ®CB | 10.0 |
| Eucarol ® TA[14] | 20.0 |
| Polymer P1[8] | 1.2 |
| Ajidew ®N50 | 3.0 |
| Water ad 100 | |
| 2.10. Hair shampoo | |
| Texapon ®SB 3 | 15.0 |
| Dehyton ®CB | 12.0 |
| Alkyl glucoside APG-600 | 4.0 |
| Polymer P1[8] | 1.2 |
| Ajidew ®N50 | 3.0 |
| Water ad 100 | |

[12]dl-2-pyrrolidone-5-carboxylic acid (AJINOMOTO)
[13]Aqueous solution of a fatty amine derivative of betaine structure; CTFA name: Coco-Betaine (approximately 31% of active substance, approximately 6.5% of NaCl) (HENKEL)
[14]Aqueous solution of sodium laureth-7-tartrate (25% of active substance) (ROL)

The invention claimed is:

1. Compositions for the treatment of hair, wherein the improvement comprises the presence in the compositions of a combination of A) from 0.1 to 10% by weight of a zwitterionic polymer consisting essentially of:

α) monomers containing quaternary ammonium groups corresponding to formula (II):

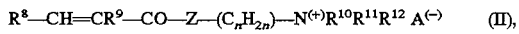

$$R^8-CH=CR^9-CO-Z-(C_nH_{2n})-N^{(+)}R^{10}R^{11}R^{12} A^{(-)} \quad (II),$$

in which $R^8$ and $R^9$ independently of one another represent hydrogen or a methyl group and $R^{10}$, $R^{11}$ and $R^{12}$ independently of one another represent alkyl groups having 1 to 4 carbon atoms, Z is an NH group or an oxygen atom, n is an integer of 2 to 5 and $A^{(-)}$ is the anion of an organic or inorganic acid and β) monomeric carboxylic acids corresponding to formula (III):

$$R^{13}-CH=CR^{14}-COOH \quad (III),$$

in which $R^{13}$ and $R^{14}$ independently of one another represent hydrogen or methyl groups, or alkali metal, alkaline earth metal, aluminum or ammonium salts of these acids, and B) from 0.1 to 15% by weight of a compound corresponding to formula (I):

in which at least one of the substituents $R^1$ to $R^3$ is a group $-COOR^4$, where $R^4$ is hydrogen, an alkali metal ion, an alkaline earth metal ion or $^+NHR^5R^6R^7$, where $R^5$ to $R^7$ independently of one another represent hydrogen, alkyl groups having 1 to 22 carbon atoms, hydroxyalkyl groups having 1 to 4 carbon atoms, alkenyl groups having 2 to 22 carbon atoms, and the remaining substituents $R^1$ to $R^3$ represent hydrogen or alkyl groups having 1 to 4 carbon atoms, based on the weight of said compositions.

2. Compositions as claimed in claim 1 wherein the monomer (α) is acrylamidopropyl trimethyl ammonium chloride and the monomer (β) is acrylic acid or an alkali metal salt thereof.

3. Compositions as claimed in claim 2, wherein compound (B) is 2-pyrrolidone-5-carboxylic acid or a salt thereof.

4. Compositions as claimed in claim 3, wherein compound (B) is the sodium salt of 2-pyrrolidone-5-carboxylic acid.

5. Compositions as claimed in claim 4, which contain the zwitterionic polymer in quantities of 0.2 to 5% by weight, based on the compositions as a whole.

6. Compositions as claimed in claim 5, which contain the compound corresponding to formula (I) in quantities of 0.5 to 10% by weight, based on the compositions as a whole.

7. Compositions as claimed in claim 6, which additionally contain a nonionic surfactant.

8. Compositions as claimed in claim 7, wherein the non-ionic surfactant is a $C_{8-22}$ alkyl mono- and oligo-glucoside in a quantity of 0.5 to 10% by weight, based on the compositions as a whole.

9. Compositions as claimed in claim 8, which are shampoos or hair rinses.

10. Compositions as claimed in claim 9, which have a pH value of 4.5 to 9.

11. A process for treating hair by applying thereto an effective amount of a composition as claimed in claim 1.

12. A process as claimed in claim 11, wherein the hair is rinsed after application of the composition.

13. Compositions as claimed in claim 1, wherein compound (B) is 2-pyrrolidone-5-carboxylic acid or a salt thereof.

14. Compositions as claimed in claim 1, which additionally contain a nonionic surfactant.

15. Compositions as claimed in claim 14, wherein said nonionic surfactant is a $C_{8-22}$ alkyl mono- and oligo-glucoside present in a quantity of 0.5 to 10% by weight, based on the compositions as a whole.

16. Compositions as claimed in claim 1, which are shampoos or hair rinses.

17. Compositions as claimed in claim 1, which have a pH value of 3.5 to 10.

* * * * *